(12) United States Patent
Butler (10) Patent No.: US 7,956,157 B2
(45) Date of Patent: Jun. 7, 2011

(54) PROCESSES USING DIVIDING WALL DISTILLATION COLUMN

(75) Inventor: James R. Butler, League City, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 12/347,922

(22) Filed: Dec. 31, 2008

(65) Prior Publication Data

US 2010/0168347 A1 Jul. 1, 2010

(51) Int. Cl.
*C08F 6/00* (2006.01)
*C07C 7/04* (2006.01)
*C08F 12/08* (2006.01)

(52) U.S. Cl. .......... 528/501; 526/68; 585/800; 585/804; 585/805; 585/806; 203/99

(58) Field of Classification Search .................... 526/68; 203/71, DIG. 19, 99; 585/802, 804, 805, 585/806, 800; 528/501
See application file for complete search history.

(56) References Cited

U.S. PATENT DOCUMENTS

| | | | |
|---|---|---|---|
| 2,471,134 A * | 5/1949 | Wright | ........................ 196/111 |
| 5,386,075 A | 1/1995 | Keil et al. | |
| 6,171,449 B1 | 1/2001 | Welch | |
| 6,407,303 B1 * | 6/2002 | O'Brien et al. | ............... 585/738 |
| 7,267,746 B1 * | 9/2007 | Harris et al. | .................. 202/160 |
| 7,339,088 B1 | 3/2008 | O'Brien et al. | |
| 2008/0289946 A1 | 11/2008 | Schultz et al. | |
| 2008/0293981 A1 | 11/2008 | Schultz et al. | |
| 2008/0293983 A1 | 11/2008 | Schultz et al. | |
| 2008/0293985 A1 | 11/2008 | Schultz et al. | |
| 2009/0306445 A1 * | 12/2009 | Gehrke | ........................ 585/435 |

FOREIGN PATENT DOCUMENTS

WO 2006136255 A2 12/2006

OTHER PUBLICATIONS

Gomez-Castro, F.I.; Segovia-Hernandez, J.G.; Hernandez, S.; Gutierrez-Antonio, C.; Briones-Ramirez, A.; "Dividing Wall Distillation Columns: Optimization and Control Properties", Chem. Eng. Tech. 2008, 31, No. 9, p. 1246-1260.

* cited by examiner

*Primary Examiner* — Fred M Teskin (74) *Attorney, Agent, or Firm* — Bradley Misley (57) ABSTRACT

A method for the separation of hydrocarbon compounds utilizing a dividing wall distillation column is described. The dividing wall distillation column enables one or more side draw stream to be removed from the dividing wall distillation column in addition to an overhead stream and a bottoms stream.

22 Claims, 6 Drawing Sheets

PROCESSES USING DIVIDING WALL DISTILLATION COLUMN

CROSS-REFERENCE TO RELATED APPLICATIONS

Not applicable.

TECHNICAL FIELD

This disclosure relates to the use of distillation to achieve impurity removal or separation of compounds from process streams. More specifically, this disclosure relates to the use of distillation to achieve separation of compounds such as ethylbenzene (EB) and polyethylbenzenes (PEB) from an alkylation process; separation of compounds such as ethylbenzene (EB), xylenes and styrene from a styrene or polystyrene production process; and separation of benzene, toluene and xylene from a mixed BTX stream.

BACKGROUND

Styrene, also known, as vinyl benzene, is an aromatic compound that can be produced in industrial quantities. The most common method of styrene production comprises the dehydrogenation of EB, which produces a product stream that includes styrene, EB and PEBs. It is desirable to reduce the amount of EB and PEBs in the polystyrene product.

Polystyrene is an aromatic polymer produced from the styrene monomer. Polystyrene is a widely used polymer found in insulation, packaging, disposable cutlery, and in foamed application such as for drinking cups. During the production of polystyrene, impurities including EB can enter with the fresh styrene feed or from a recycle stream. The EB can exit the process as a purge stream, or in the composition of the polystyrene product. It can be desirable to reduce the amount of EB in the polystyrene product.

Separation of EB from the crude styrene product or in the purge stream of a polystyrene process can be difficult due to the similar boiling points of EB and styrene. The use multiple distillation columns is the typical means of component separation.

The alkylation of benzene to produce ethylbenzene is a common commercial reaction included in the production of styrene. The separation of the products of such a reaction is typically accomplished by a series of distillation steps. Likewise the separation of product streams such as BTX, a mixture of benzene, toluene and xylene, is also typically accomplished by a series of distillation steps.

The use of process schemes incorporating multiple distillation columns can be costly and inefficient. Thus, it would be desirable accomplish component separation utilizing a reduced number of distillation columns by a method that is more economically viable.

SUMMARY

Disclosed herein is a method for the separation of hydrocarbon compounds that includes obtaining a first stream comprising hydrocarbon compounds and sending at least a portion of the first stream to a dividing wall distillation column comprising a dividing wall. An overhead stream and a bottoms stream are removed from the dividing wall distillation column along with a side draw stream. The first stream enters the dividing wall distillation column on an opposing side as the side draw stream and the first stream inlet and the side draw stream outlet are separated by the dividing wall. The first stream can be fed to the dividing wall distillation column at a location above where the side draw stream is taken. A second side draw stream can be removed from the dividing wall distillation column at a point lower than the side draw stream and is also on an opposing side as the first stream.

The first stream can be produced from a first reaction zone. At least a portion of the overhead stream, side draw stream or bottoms stream can be recycled as feed to the first reaction zone. The first stream can be a reactor effluent stream from a polystyrene reaction zone where the side draw stream comprises styrene that can be recycled to the polystyrene reaction zone. At least a portion of the first stream can be recycled to the polystyrene reaction zone. The overhead stream can comprise ethylbenzene.

The first reaction zone can produce a first stream comprising styrene and can be an ethylbenzene dehydrogenation reaction zone.

The first reaction zone can be a benzene alkylation reaction zone that produces a first stream comprising ethylbenzene where the overhead stream comprises benzene, the side draw stream comprises ethylbenzene and the bottoms stream comprises polyethylbenzene. The bottoms stream can be fed to a transalkylation reaction zone and produce a second stream that has a lower polyethylbenzene content than the bottoms stream. A portion of the second product stream can be fed to the dividing wall distillation column.

A second side draw stream can be removed from the dividing wall distillation column at a point lower than the side draw stream. The second side draw stream can comprise polyethylbenzene and be fed to a transalkylation reaction zone to produce a second stream that has lower polyethylbenzene content than the second side draw stream. All or a portion of the second product stream can be fed to the dividing wall distillation column.

In one embodiment the first stream comprises at least two of benzene, toluene, xylene or ethylbenzene and the dividing wall distillation column can produce an overhead stream comprising benzene, a side draw stream comprising toluene and a bottoms stream comprising xylene. A second side draw stream from the dividing wall distillation column can be removed at a point lower than the side draw stream, wherein the second side draw stream comprises polyethylbenzene.

Another embodiment of the invention is a method of polystyrene production by feeding a stream comprising styrene to a polystyrene reaction zone, wherein a stream comprising polystyrene is removed and a reactor effluent stream is removed. At least a portion of the reactor effluent stream is sent to a dividing wall distillation column where an overhead stream, a bottoms stream and a side draw stream are removed from the dividing wall distillation column, the side draw stream comprising styrene. The feed stream can comprise styrene mixed with a solvent prior to entering the polystyrene reaction zone, the solvent comprising paraffin boiling in the range of from 135° C. to 150° C. The reactor effluent is fed to the dividing wall distillation column at a location above where the side draw stream is taken. The side draw stream can be recycled to the polystyrene reaction zone. A portion of the reactor effluent stream can be recycled to the polystyrene reaction zone. The reactor effluent stream can include styrene and ethylbenzene. The overhead stream can include ethylbenzene.

Yet another embodiment is a method of styrene production that includes obtaining a first product stream from a styrene reaction zone and sending at least a portion of the first product stream to a dividing wall distillation column. An overhead stream, bottoms stream and a side draw stream are removed from the dividing wall distillation column. The first product stream can be fed to the dividing wall distillation column at a location above where the side draw stream is taken. The side draw stream can include styrene and the overhead stream can include ethylbenzene. At least a portion of the overhead stream can be recycled to the styrene reaction zone.

Still another embodiment is a method of ethylbenzene production that includes obtaining a first product stream from an alkylation reaction zone and sending at least a portion of the first product stream to a dividing wall distillation column. An overhead stream, bottoms stream and a side draw stream are removed from the dividing wall distillation column. The first product stream can be fed to the dividing wall distillation column at a location above where the side draw stream is taken. The side draw stream can include ethylbenzene and the overhead stream can include benzene. At least a portion of the overhead stream can be recycled to the alkylation reaction zone. The bottoms stream can include polyethylbenzene and at least a portion of the bottoms stream can be fed to a transalkylation reaction zone to produce a second product stream that has reduced polyethylbenzene content than the bottoms stream. At least a portion of the second product stream can be fed to the dividing wall distillation column.

Disclosed herein is a method for production of polystyrene, wherein a dividing wall distillation column is used for impurity removal and styrene recovery from the reactor effluent. More specifically, disclosed herein is a method for production of polystyrene wherein a polystyrene reactor effluent is sent to a dividing wall distillation column, wherein the dividing wall distillation column produces a light cut stream, a heavy cut stream, and a recycle stream containing styrene.

DETAILED DESCRIPTION

Disclosed herein are methods for the separation of hydrocarbon compounds that includes a dividing wall distillation column comprising a dividing wall. The dividing wall vertically bisects a portion of the interior of the distillation column but does not extend to the top or bottom sections of the column, thus enabling the column to be refluxed and reboiled similar to a conventional column. The dividing wall provides a fluid impermeable baffle separating the interior of the column. The inlet to the column is located on one side of the dividing wall while one or more side draws are located on the opposing side. The dividing wall enables the side of the column that does not have the inlet to function in a more stable manner with minimal effect from fluctuations in inlet flow rates, conditions or composition. This increased stability enables the column to be designed and operated in a manner that allows one or more side draw streams to be removed from the column having different compositions from either the overhead stream or the bottoms stream.

The ability to make three or more product streams from a single column can enable component separation with fewer distillation columns and possibly reduced capital costs. The dividing wall distillation column can be used as a sole distillation column or multiple dividing wall distillation column can be used, either in series or parallel arrangements. The dividing wall distillation column can also be used in conjunction with one or more conventional distillation column. Embodiments of the present invention can be particularly applicable when the optimum feed location to the column is above the optimum side draw location. If the feed location is above the side draw location in a conventional distillation column, the downward flow of the liquid feed within the column will have a significant effect on the side draw composition. Variations in the feed flow rate, conditions or composition of the feed stream will alter the side draw composition and make the production of a stable side draw stream very difficult to achieve.

Disclosed herein is a method for production of polystyrene wherein a polystyrene reactor produces one stream comprising polystyrene and a second stream of reactor effluent, wherein the reactor effluent is sent to a dividing wall distillation column, wherein the dividing wall distillation column can produce a light cut, heavy cut, and styrene recycle streams.

The styrene feed to a polystyrene reactor may include contaminants including ethyl-benzene. Ethyl-benzene, as well as other aromatics, is typically allowed to build up in the process in order to create a dilutant for the reaction. A dilutant can be utilized to absorb the heat of reaction, and thereby control the polymerization reaction rate and prevent a runaway reaction. Other aromatic impurities may include ortho-xylene, meta-xylene, cumene, n-propylbenzene and MPET and as a group herein referred to as other aromatic impurities.

It can be advantageous to reduce the content of ethyl-benzene in the polystyrene product. The amount of ethyl-benzene contained in the polystyrene pellets is proportional to the amount of ethyl-benzene in the reactor, approximately one pound of ethyl-benzene leaves in the pellets for every thousand pounds of ethyl-benzene that leaves the reactor.

The styrene feed can also include a solvent, for example, Isane 130. In an illustrative example, the styrene feed may comprise between 75 and 99.5 weight percent styrene, from 0 to 20 weight percent Isane 130, and 10 ppm to 5000 ppm ethyl-benzene. As a further example, the styrene feed may comprise between from 85 to 95 weight percent styrene, from 7 to 12 weight percent Isane 130, and 100 ppm to 1000 ppm ethyl-benzene.

The solvent, Isane 130, is a commercial name for a solvent sold by TOTAL Petrochemicals USA, Inc. The solvent is composed of paraffins having a boiling point range of between about 135 to about 150 degrees Celsius. The composition of Isane 130, as determined by ASTM D86, is represented in Table 1 below.

TABLE 1

| Component | Mass Fraction |
| --- | --- |
| 2,4-DIMETHYLHEXANE | 0.022054 |
| 2,3,3-TRIMETHYLPENTANE | 1.10E−15 |
| 3-METHYLHEPTANE | 0 |

TABLE 1-continued

| Component | Mass Fraction |
|---|---|
| N-OCTANE | 0 |
| 2,4,4-TRIMETHYLHEXANE | 0.13726 |
| 2,2,3,4,-TETRAMETHYLPENTANE | 0.19991 |
| 2,6-DIMETHYLHEPTANE | 0.31968 |
| 2,2,3,3-TETRAMETHYLPENTANE | 0.23961 |
| 3-METHYLOCTANE | 0.051423 |
| N-NONANE | 0 |
| 3,3,5-TRIMETHYLHEPTANE | 0 |
| 2,6-DIMETHYLOCTANE | 0.0002 |
| 4-METHYLNONANE | 0.000353 |
| DECANE | 0.029509 |

Isane 130 can be a good solvent for a polystyrene process, because a bulk of the solvent boils between styrene and ethyl-benzene and therefore increases the relative volatility between styrene and ethyl-benzene. Thus, the addition of Isane 130 solvent in the styrene feed composition can make the task of separating styrene and ethyl-benzene easier.

A polystyrene reaction zone produces polystyrene and an effluent stream. A portion of the effluent stream can be taken as a purge stream to maintain the composition of aromatics other than styrene in the process. The effluent stream can be recycled to the inlet of the polystyrene reaction zone and/or added with fresh styrene feed to the reactor.

In accordance with an embodiment of the invention, at least a portion of the reactor effluent can be sent to a distillation column for impurity removal. According to one embodiment of the invention, 0.01 to 99.99 weight percent is recycled to the polystyrene reaction zone, while the remaining portion is sent to a distillation column. According to another embodiment of the invention, 50 to 95 weight percent of the effluent is recycled, while the remaining portion is sent to a distillation column. According to yet another embodiment, 75 to 95 weight percent is recycled to the polystyrene reaction zone, while the remaining portion is sent to a distillation column.

In accordance with another embodiment of the invention, all of the reactor effluent is sent to a distillation column.

In accordance with the invention, the distillation column comprises an interior dividing wall and can be referred to as a dividing wall distillation column. In this embodiment, the feed tray and the side draw tray are on opposite sides of the dividing wall. In this dividing wall column arrangement, the dividing wall acts as a barrier to prevent the entering feed from affecting the composition of the side draw stream. This arrangement allows for the feed tray to be in a position above the side draw tray. Therefore, the dividing wall column arrangement allows for a sidedraw to be taken from the same column that a feed stream enters.

According to an embodiment of the invention, the dividing wall recovery column comprises between 20 and 100 equilibrium stages, or trays. According to another embodiment, the dividing wall recovery column comprises between 30 and 90 trays. According to yet another embodiment, the dividing wall recovery column comprises between 40 and 80 trays. The column may contain any suitable type packing or trays such as non-limiting examples sieve or bubble trays.

According to the embodiments, the feed tray is located on the opposite side of the dividing wall as the side draw tray. According to an embodiment, the feed tray is located at or above the side draw tray. According to another embodiment, the feed tray is located below the side draw tray.

The invention disclosed herein can be utilized for separating ethyl-benzene from styrene. According to embodiments of this styrene separation process, a styrene and ethyl-benzene mixture is fed to a dividing wall distillation column. The dividing wall distillation column separates the styrene and ethyl-benzene mixture into up to four separate streams. These four separate streams comprise an overhead product comprising ethyl-benzene, a side draw product comprising styrene product, a lower side draw stream comprising polyethylbenzene, and a bottoms residue stream.

In accordance with the embodiments, the styrene and ethyl-benzene mixture fed to the dividing wall distillation column is obtained from the product stream of a styrene production process. In an embodiment, a styrene reactor product is sent directly to the dividing wall distillation column for styrene recovery.

The invention disclosed herein can be utilized for separating aromatic compounds such as mixtures of benzene, toluene, xylenes and ethylbenzene. According to embodiments of this aromatic separation process, an aromatic mixture is fed to a dividing wall distillation column. The dividing wall distillation column separates the components into up to four separate streams. These four separate streams can comprise an overhead product comprising benzene, a side draw product comprising toluene, and a bottoms stream of xylenes and ethylbenzene. An alternate aromatic separation can be the separation of a BTX (benzene-toluene-xylene) stream into an overhead product comprising benzene, a side draw product comprising toluene, and a bottoms stream of xylene.

The invention disclosed herein can be utilized for separating products from an alkylation reaction, such as the alkylation of benzene to ethylbenzene. The products can include benzene, ethylbenzene and polyethylbenzenes. The dividing wall distillation column separates the components into up to four separate streams. These four separate streams can comprise an overhead product comprising benzene, an upper side draw product comprising ethylbenzene, a lower side draw product comprising polyethylbenzenes and a bottoms stream of heavier components such as tetraethylbenzene.

DETAILED DESCRIPTION OF THE DRAWINGS

Figure 1:
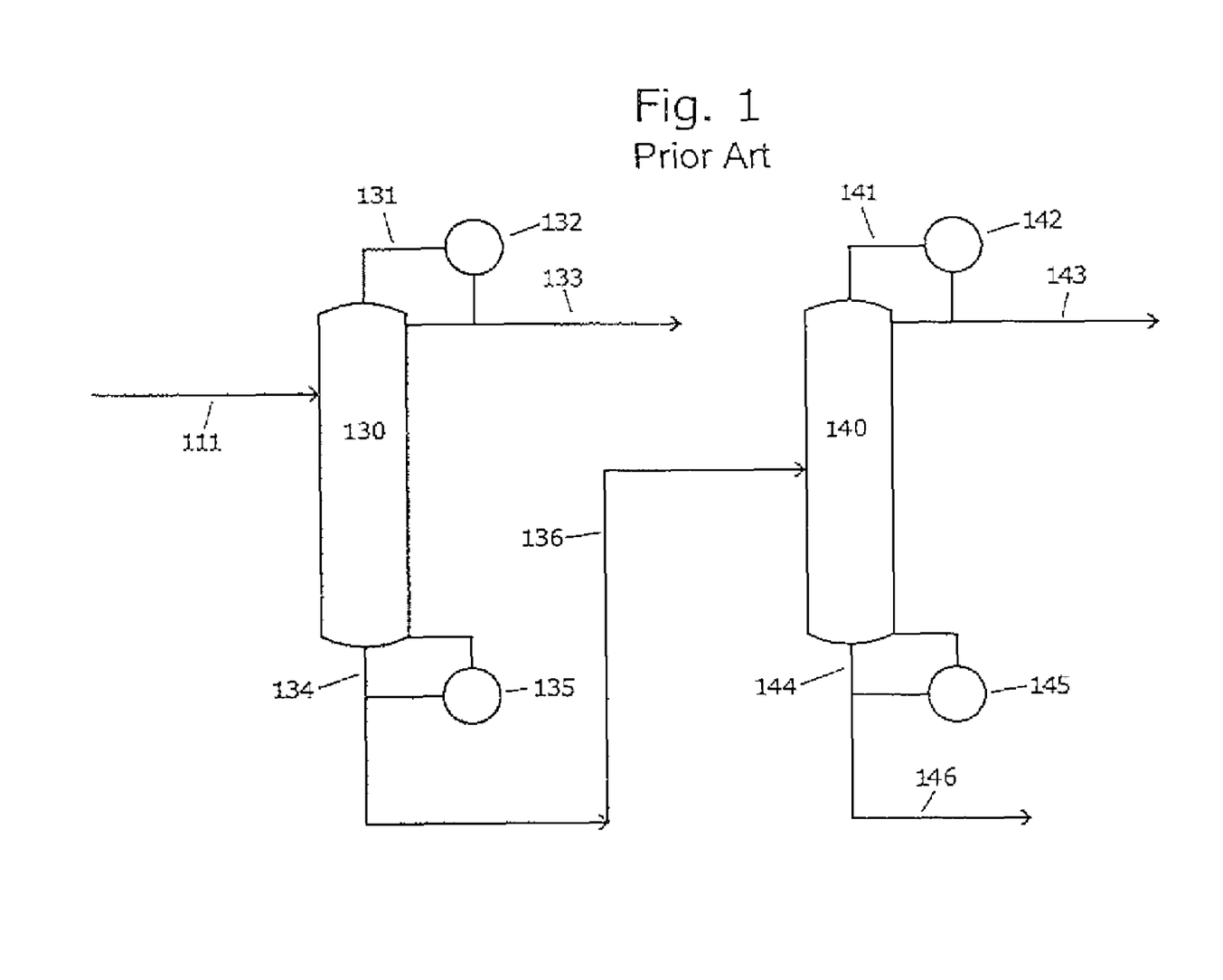
FIG. 1 shows a prior art distillation separation process with multiple distillation columns not having a side draw.

FIG. 1 depicts a separation process utilizing two distillation columns for the separation of components according to prior art. The first distillation column (130) separates an inlet stream (111) into an overhead stream (131) and a bottoms stream (134) that will comprise styrene. The overhead (131) is condensed in condenser (132), resulting in stream (133). A portion of the condensed stream (133) can be refluxed to the first distillation column (130). A portion of bottoms stream (134) is sent back into the column via reboiler (135), while the remaining bottoms is withdraw in line (136).

The bottoms stream (136) is sent to a second distillation column (140) that produces an overhead stream (141) and a bottoms stream (144). The overhead (141) is condensed in condenser (142), resulting in stream (143), a portion of which can be refluxed to the second distillation column (140). A portion of bottoms stream (144) is sent back into the column via reboiler (145), while the remaining bottoms is withdraw in line (146).

Figure 2:
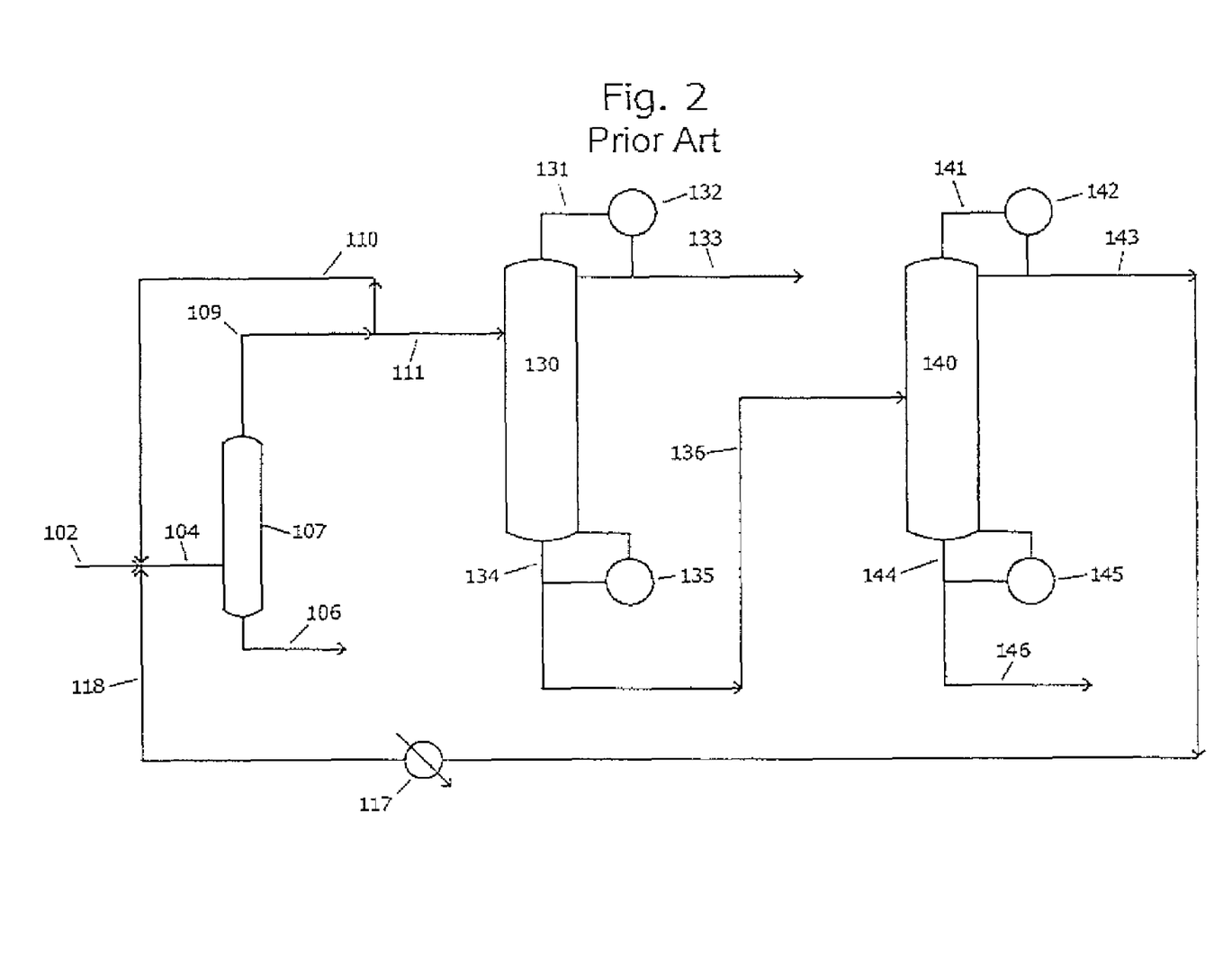
FIG. 2 shows a polystyrene process having a purge stream separated using multiple distillation columns not having a side draw.

FIG. 2 depicts a polystyrene process utilizing two distillation columns for the treatment of the reaction effluent stream according to prior art. Styrene feed (102) is mixed with a styrene recycle stream (118), resulting in a mixed polystyrene reactor feed (104).

The polystyrene reactor (107) produces a polystyrene product (106) and an effluent stream (109).

A portion of the effluent (109) can be purged in stream (110) or recycled back to the mixed polystyrene reactor feed (104). The remaining effluent (111) that is not purged or recycled is sent to a first distillation column (130). The first distillation column (130) separates effluent (111) into an overhead stream (131) and a bottoms stream (134) that will comprise styrene. The overhead (131) is condensed in condenser (132), resulting in stream (133). A portion of bottoms stream (134) is sent back into the column via reboiler (135), while the remaining bottoms is withdraw in line (136).

The bottoms stream (136) is sent to a second distillation column (140) that produces an overhead stream (141) that comprises styrene and a bottoms stream (144). The overhead (141) is condensed in condenser (142), resulting in recycle stream (143). A portion of bottoms stream (144) is sent back into the column via reboiler (145), while the remaining bottoms is withdraw in line (146).

The recycle stream (143), comprising styrene, can be sent to a heat exchanger (117) to obtain a liquid styrene stream (118), which is then mixed with the styrene feed (102).

Figure 3:
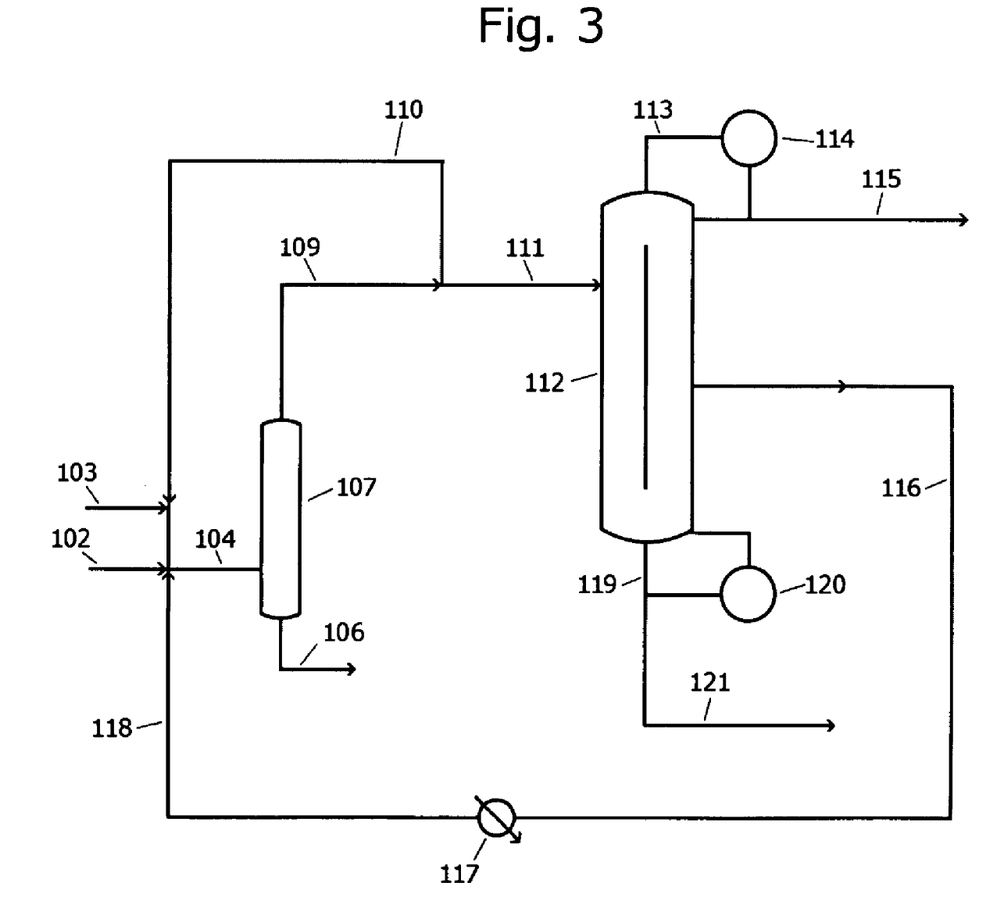
FIG. 3 shows a polystyrene process having a purge stream separated using a dividing wall distillation column having a side draw.

FIG. 3 depicts an embodiment of the invention, wherein a single dividing wall recovery column is applied to the polystyrene process. Styrene feed (102) is mixed with Isane solvent (103), an effluent recycle stream (110) and a styrene recycle stream (118), resulting in a mixed polystyrene reactor feed (104).

The polystyrene reactor (107) produces a polystyrene product (106) and an effluent stream (109).

A portion of the reactor effluent stream (109) is then optionally sent to a purge or a recycle in stream (110). The remaining effluent (111) that is not purged or recycled is sent to the dividing wall distillation column (112). The dividing wall distillation column (112) separates effluent (111) into an overhead stream (113), a styrene recycle stream (116), and a bottoms stream (119). The overhead (113) is condensed in condenser (114), resulting in stream (115). The recycle stream (116), comprising styrene, can be sent to a heat exchanger (117) to obtain a liquid styrene stream (118), that is then mixed with the styrene feed (102) and Isane solvent (103). A portion of bottoms stream (119) is sent back into the column via reboiler (120), while the remaining bottoms is withdraw in line (121).

Figure 4:
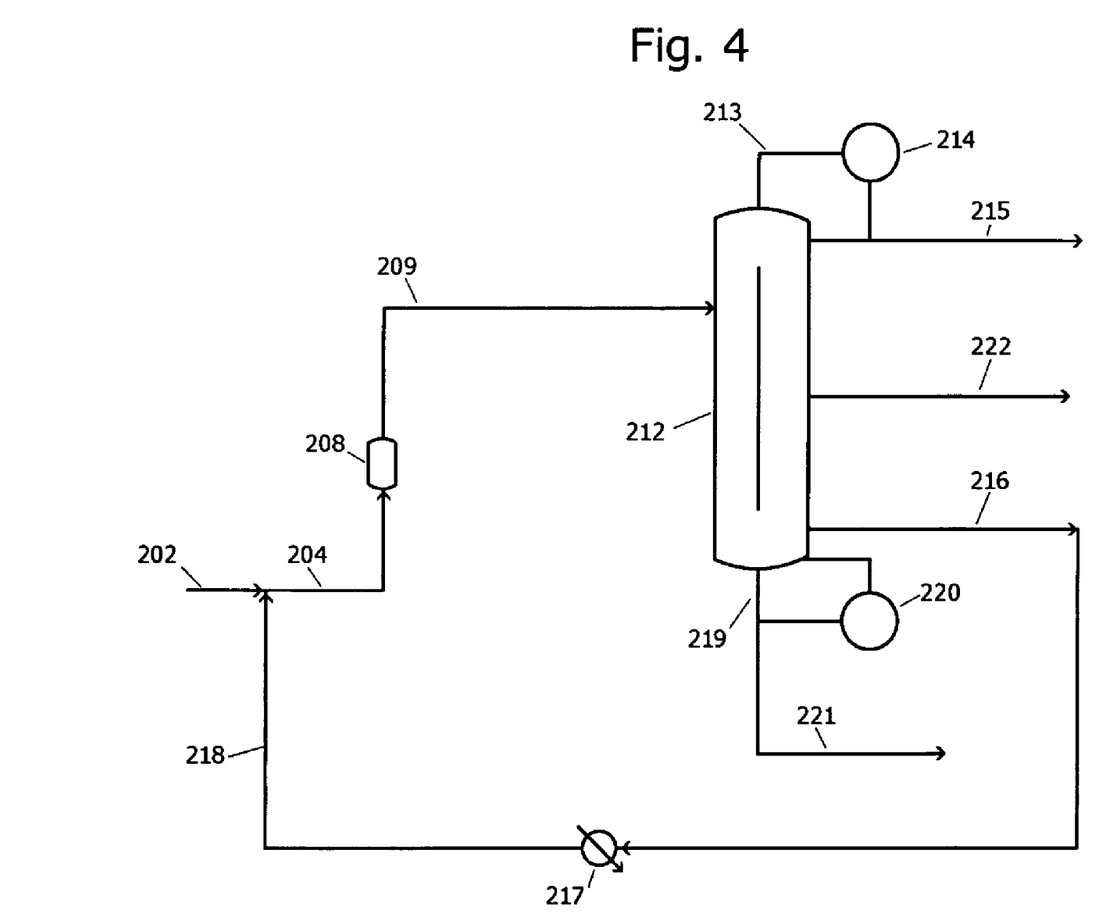
FIG. 4 shows a production process incorporating a dividing wall distillation column having two side draws, one side draw being a recycle stream.

FIG. 4 illustrates an embodiment of the invention, wherein the dividing wall column distillation is used to produce two side draw streams. A feed (202) is mixed with a recycle stream (218), resulting in a mixed reactor feed (204) that is fed to reactor (208). The reactor (208) produces product stream (209).

The product stream (209) is then sent to a dividing wall distillation column (212) that separates product stream (209) into an overhead stream (213), an upper side draw stream (222), a lower side draw recycle stream (216), and a bottoms residue stream (219). The overhead (213) is condensed in condenser (214), resulting in stream (215). The recycle stream (216) can be sent to a heat exchanger (217) to obtain recycle stream (218), that is then mixed with the feed (202). A portion of bottoms residue stream (219) is sent back into the column via reboiler (220), while the remaining bottoms residue is withdraw in line (221). Optionally any of the streams (215, 222, 216 or 221) can be used as the recycle stream depending on the particular components being separated and the particular products being produced.

Figure 5:
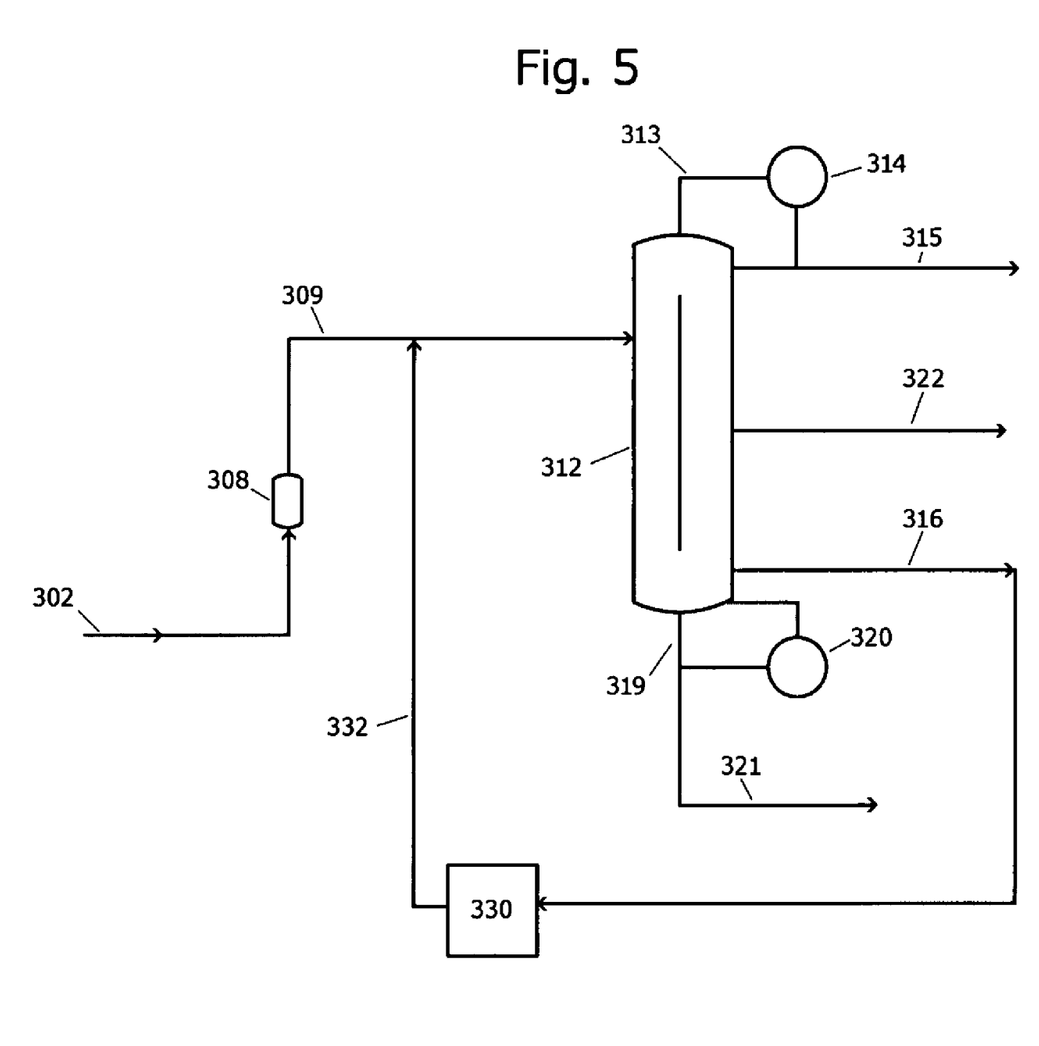
FIG. 5 shows a production process incorporating a dividing wall distillation column having two side draws, one side draw being a recycle stream having a second separate reaction zone.

FIG. 5 illustrates an embodiment of the invention of an alkylation reaction to produce ethylbenzene, wherein the dividing wall column distillation is used to produce two side draw streams. A feed (302) comprising benzene and ethylene is fed to alkylation reactor (308). The reactor (308) produces product stream (309) comprising benzene, ethylbenzene and polyethylbenzene.

The product stream (309) is then sent to a dividing wall distillation column (312) that separates product stream (309) into an overhead stream (313), an upper side draw stream (322) comprising ethylbenzene product, a lower side draw recycle stream (316) comprising polyethylbenzene, and a bottoms residue stream (319). The overhead (313) is condensed in condenser (314), resulting in stream (315) that includes benzene and lighter components. Stream (315) may be recycled (not shown) back to the feed stream (302). The lower side draw stream (316) comprising polyethylbenzene can be a recycle stream sent to a transalkylation reactor (330) to obtain recycle stream (332) that has a lower polyethylbenzene content than the lower side draw stream (316), that is then mixed with the product stream (309) and sent to dividing wall distillation column (312). A portion of bottoms residue stream (319) is sent back into the column via reboiler (320), while the remaining bottoms residue contains heavier components such as tetraethylbenzene is withdraw in line (321).

Figure 6:
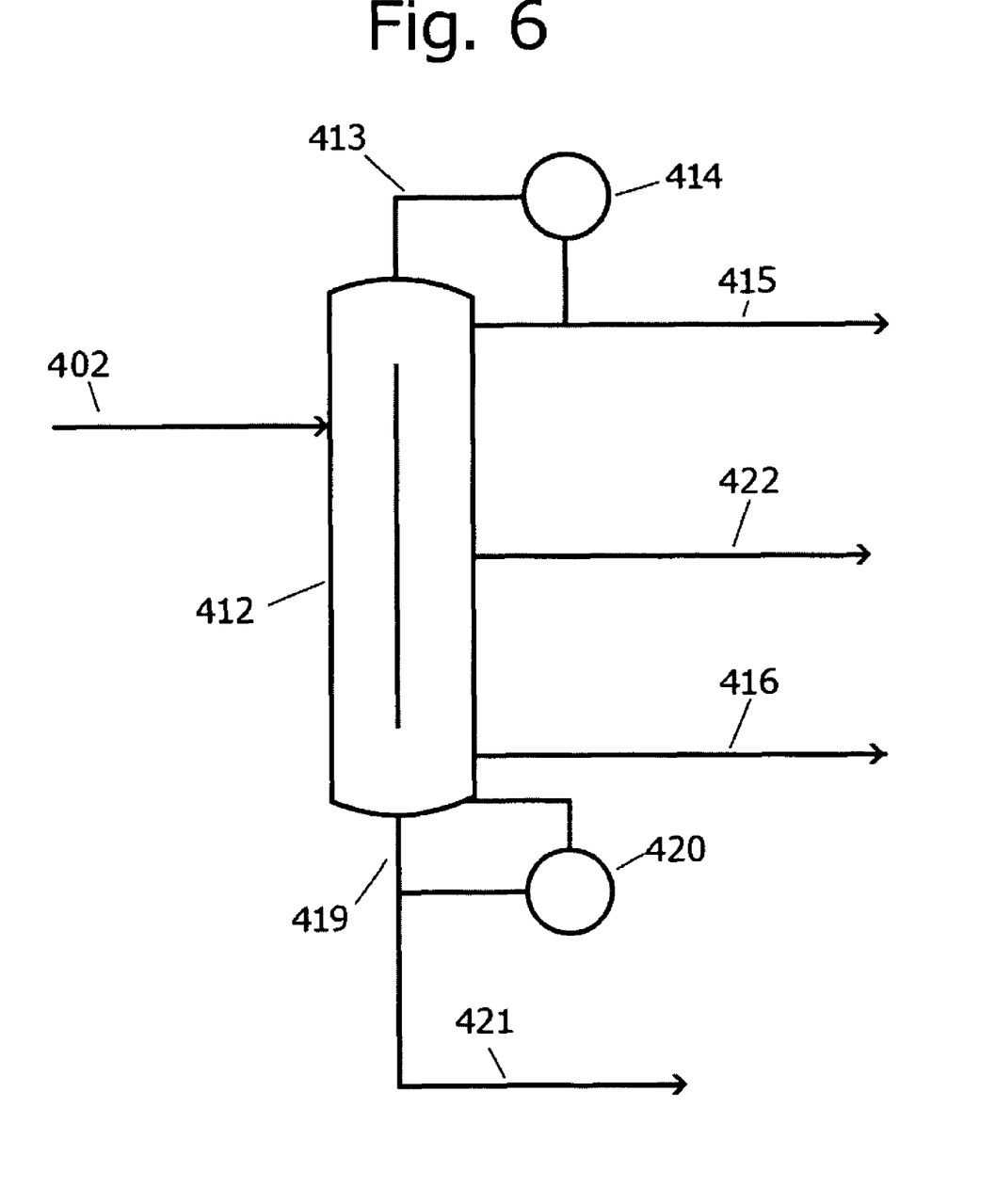
FIG. 6 is a schematic illustration of a dividing wall distillation column having two side draws along with an overhead and bottoms outlet streams.

FIG. 6 illustrates a dividing wall distillation column (412) that separates a mixed stream (402) into an overhead stream (413), an upper side draw stream (422), a lower side draw stream (416), and a bottoms stream (419). The mixed stream (402) is fed to the dividing wall distillation column (412) on the opposite side of the vertically positioned dividing wall from the side draw streams (422) (416). The overhead (413) is condensed in condenser (414), resulting in stream (415), a portion of which will typically be used as a reflux stream for the dividing wall distillation column (412). A portion of bottoms residue stream (419) is sent back into the column via reboiler (420), while the remaining bottoms residue is withdraw in line (421).

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

As used herein, "parallel" or "parallel arrangement" is defined to mean that the components are not arranged in series and that each component separately processes a portion of the stream. As such, the components do not have to be aligned in a true physical parallel manner with respect to each other.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

The invention claimed is:

1. A method for the separation of hydrocarbon compounds comprising:
    obtaining a first stream comprising hydrocarbon compounds, wherein the first stream is a reactor effluent stream from a polystyrene reaction zone;
    sending at least a portion of the first stream to a dividing wall distillation column comprising a dividing wall;
    removing an overhead stream and a bottoms stream from the dividing wall distillation column; and removing a side draw stream from the dividing wall distillation column;

wherein the first stream enters the dividing wall distillation column on an opposing side as the side draw stream, separated by the dividing wall.

2. The method of claim 1, wherein the side draw stream comprises styrene.

3. The method of claim 2, wherein the side draw stream is recycled to the polystyrene reaction zone.

4. The method of claim 1, wherein at least a portion of the first stream is recycled to the polystyrene reaction zone.

5. The method of claim 1, wherein the overhead stream comprises ethylbenzene.

6. A method for the separation of hydrocarbon compounds comprising:
   obtaining a first stream comprising hydrocarbon compounds, wherein the first stream is produced from a first reaction zone that produces the first stream comprising styrene;
   sending at least a portion of the first stream to a dividing wall distillation column comprising a dividing wall;
   removing an overhead stream and a bottoms stream from the dividing wall distillation column; and
   removing a side draw stream from the dividing wall distillation column;
wherein the first stream enters the dividing wall distillation column on an opposing side as the side draw stream, separated by the dividing wall.

7. The method of claim 6, wherein the first reaction zone is an ethylbenzene dehydrogenation reaction zone.

8. A method for the separation of hydrocarbon compounds comprising:
   obtaining a first stream comprising at least toluene and one of benzene, xylene or ethylbenzene;
   sending at least a portion of the first stream to a dividing wall distillation column comprising a dividing wall;
   removing an overhead stream and a bottoms stream from the dividing wall distillation column; and
   removing a side draw stream from the dividing wall distillation column, wherein the side draw stream comprises toluene;
wherein the first stream enters the dividing wall distillation column on an opposing side as the side draw stream, separated by the dividing wall.

9. A method for the separation of hydrocarbon compounds comprising:
   obtaining a first stream comprising at least xylene and at least one of benzene, toluene, or ethylbenzene;
   sending at least a portion of the first stream to a dividing wall distillation column comprising a dividing wall;
   removing an overhead stream and a bottoms stream from the dividing wall distillation column, wherein the bottoms stream comprises xylene; and
   removing a side draw stream from the dividing wall distillation column;
wherein the first stream enters the dividing wall distillation column on an opposing side as the side draw stream, separated by the dividing wall.

10. A method of polystyrene production comprising:
    feeding a stream comprising styrene to a polystyrene reaction zone, wherein a stream comprising polystyrene is removed and a reactor effluent stream is removed;
    sending at least a portion of the reactor effluent stream to a dividing wall distillation column;
    removing an overhead stream and a bottoms stream from the dividing wall distillation column; and
    removing a side draw stream comprising styrene from the dividing wall distillation column.

11. The method of claim 10, wherein the feed stream comprising styrene is mixed with a solvent prior to entering the polystyrene reaction zone.

12. The method of claim 11, wherein the solvent comprises paraffin boiling in the range of from 135° C. to 150° C.

13. The method of claim 10, wherein the reactor effluent is fed to the dividing wall distillation column at a location above where the side draw stream is taken.

14. The method of claim 10, wherein the side draw stream is recycled to the polystyrene reaction zone.

15. The method of claim 10, wherein at least a portion of the reactor effluent stream is recycled to the polystyrene reaction zone.

16. The method of claim 10, wherein the reactor effluent stream comprises styrene and ethylbenzene.

17. The method of claim 10, wherein the overhead stream comprises ethylbenzene.

18. A method of styrene production comprising:
    obtaining a first product stream from a styrene reaction zone;
    sending at least a portion of the first product stream to a dividing wall distillation column;
    removing an overhead stream and a bottoms stream from the dividing wall distillation column; and
    removing a side draw stream from the dividing wall distillation column.

19. The method of claim 18, wherein the first product stream is fed to the dividing wall distillation column at a location above where the side draw stream is taken.

20. The method of claim 18, wherein the side draw stream comprises styrene.

21. The method of claim 18, wherein the overhead stream comprises ethylbenzene.

22. The method of claim 18, wherein at least a portion of the overhead stream is recycled to the styrene reaction zone.

* * * * *